United States Patent
Jang et al.

(10) Patent No.: US 11,935,236 B2
(45) Date of Patent: Mar. 19, 2024

(54) APPARATUS AND METHOD FOR INTERLOCKING LESION LOCATIONS BETWEEN A GUIDE IMAGE AND A 3D TOMOSYNTHESIS IMAGES COMPOSED OF A PLURALITY OF 3D IMAGE SLICES

(71) Applicant: LUNIT INC., Seoul (KR)

(72) Inventors: Jung Hee Jang, Suwon-si (KR); Do Hyun Lee, Seoul (KR); Woo Suk Lee, Yongin-si (KR); Rae Yeong Lee, Suwon-si (KR)

(73) Assignee: Lunit Inc., Seoul (KR)

( * ) Notice: Subject to any disclaimer, the term of this patent is extended or adjusted under 35 U.S.C. 154(b) by 0 days.

(21) Appl. No.: 18/093,162

(22) Filed: Jan. 4, 2023

(65) Prior Publication Data

US 2023/0237653 A1    Jul. 27, 2023

(30) Foreign Application Priority Data

Jan. 21, 2022    (KR) .................. 10-2022-0009411
Aug. 23, 2022    (KR) .................. 10-2022-0105464

(51) Int. Cl.
 G06T 7/00     (2017.01)
 G06T 3/40     (2006.01)
 G06T 15/00    (2011.01)

(52) U.S. Cl.
 CPC .............. *G06T 7/0012* (2013.01); *G06T 3/40* (2013.01); *G06T 15/00* (2013.01); *G06T 2207/10072* (2013.01); *G06T 2207/30096* (2013.01); *G06T 2210/41* (2013.01)

(58) Field of Classification Search
 CPC ......... G06T 7/0012; G06T 3/40; G06T 15/00; G06T 2207/10072; G06T 2207/10132; G06T 2207/30096; G06T 2210/41
 See application file for complete search history.

(56) References Cited

U.S. PATENT DOCUMENTS

| | | | |
|---|---|---|---|
| 8,634,622 B2 | 1/2014 | Woods et al. | |
| 8,687,867 B1 | 4/2014 | Collins et al. | |
| 8,983,156 B2 | 3/2015 | Periaswamy et al. | |
| 10,916,010 B2 * | 2/2021 | Sugahara | A61B 6/502 |
| 11,205,265 B2 | 12/2021 | Hall et al. | |
| 2003/0007598 A1 * | 1/2003 | Wang | A61B 6/463 |
| | | | 378/37 |
| 2010/0135558 A1 * | 6/2010 | Ruth | G06T 19/20 |
| | | | 715/866 |
| 2015/0052471 A1 * | 2/2015 | Chen | A61B 6/466 |
| | | | 715/771 |
| 2018/0158228 A1 | 6/2018 | Karssemeijer et al. | |
| 2020/0054300 A1 | 2/2020 | Kreeger et al. | |

FOREIGN PATENT DOCUMENTS

| | | |
|---|---|---|
| JP | 2009-207545 A | 9/2009 |
| JP | 2014-195729 A | 10/2014 |
| JP | 5702041 B2 | 4/2015 |
| JP | 6429958 B2 | 11/2018 |
| KR | 10-1923962 B1 | 11/2018 |

* cited by examiner

*Primary Examiner* — Jon Chang
(74) *Attorney, Agent, or Firm* — Sughrue Mion, PLLC

(57) ABSTRACT

Provided are a method and an apparatus for interlocking a lesion location between a 2D medical image and 3D tomosynthesis images including a plurality of 3D image slices.

11 Claims, 15 Drawing Sheets

APPARATUS AND METHOD FOR INTERLOCKING LESION LOCATIONS BETWEEN A GUIDE IMAGE AND A 3D TOMOSYNTHESIS IMAGES COMPOSED OF A PLURALITY OF 3D IMAGE SLICES

CROSS-REFERENCE TO RELATED APPLICATION

This application claims priority from Korean Patent Application No. 10-2022-0009411 filed on Jan. 21, 2022, and Korean Patent Application No. 10-2022-0105464 filed on Aug. 23, 2022, in the Korean Intellectual Property Office, the disclosure of which is incorporated herein by reference in its entirety.

BACKGROUND

1. Field

The present disclosure relates to an apparatus and a method for interlocking a lesion location between a guide image and three dimensional (3D) tomosynthesis images comprising a plurality of 3D image slices.

2. Description of the Related Art

Conventional cancer diagnosis mainly uses two dimensional (2D) medical images by obtaining X-ray images of body parts such as the breast and the chest in a single direction. However, in a 2D medical image, the tumor in a region of interest overlaps the normal tissue. Therefore, there are many difficulties in detection of micro-calcifications, which is an important factor in early diagnosis of cancer.

Therefore, for early detection of cancer, the 3D tomosynthesis has been developed, which supplements the method of using 2D medical images by imaging body parts from various angles and synthesizing obtained tomograph images for improved diagnosis.

Since the 3D tomosynthesis images reconstruct a 3-dimensional image, the overlapping area of the tissue is reduced, and the tumor may be easily distinguished from the normal tissue of the body parts. Therefore, the 3D tomosynthesis images method exhibits high tumor detection ability.

In this regard, there is a need for a technology for more efficiently reading a lesion by using 2D medical images and 3D tomosynthesis images together.

The above-stated background art is technical information possessed by the inventor for the derivation of the present disclosure or obtained in the process of derivation of the present disclosure and may not necessarily be a known technique disclosed to the general public prior to the filing of the present disclosure.

SUMMARY

Provided are an apparatus and a method for interlocking a lesion location between a guide image and 3D tomosynthesis images comprising a plurality of 3D image slices. The problem to be solved by the present disclosure is not limited to the above-stated problems, and other problems and advantages of the present disclosure not mentioned may be understood by the following description and more clearly understood by the embodiments of the present disclosure. Also, it will be appreciated that the problems and advantages to be solved by the present disclosure may be realized by means and combinations thereof indicated in the claims.

Additional aspects will be set forth in part in the description which follows and, in part, will be apparent from the description, or may be learned by practice of the presented embodiments of the disclosure.

According to an embodiment, provided is a method of interlocking a lesion location between a guide image and 3D tomosynthesis image including a plurality of 3D image slices, the method including: receiving a medical image set corresponding to at least one patient from a first server; identifying a patient being read in response to generation of a pre-set trigger signal; determining a certain medical image set corresponding to an identified patient; identifying at least one 3D image slice constituting 3D tomosynthesis images from among a plurality of medical images included in the certain medical image set; and providing the identified 3D image slice and a guide image which is a 2D medical image corresponding to the 3D tomosynthesis images to be simultaneously displayed, wherein a lesion location is displayed on the identified 3D image slice and the guide image and interlocked between the identified 3D image slice and the guide image.

According to another embodiment, provided is a server for interlocking a lesion location between a guide image and 3D tomosynthesis images including a plurality of 3D image slices, the server including: a memory in which at least one program is stored; and at least one processor operated by executing the at least one program, wherein the at least one processor is configured to receive a medical image set corresponding to at least one patient from a first server, identify a patient being read in response to generation of a pre-set trigger signal; determine a certain medical image set corresponding to an identified patient, identify at least one 3D image slice constituting 3D tomosynthesis images from among a plurality of medical images included in the certain medical image set, and provide the identified 3D image slice and a guide image which is a 2D medical image corresponding to the 3D tomosynthesis images to be simultaneously displayed, and a lesion location is displayed on the identified 3D image slice and the guide image and interlocked between the identified 3D image slice and the guide image.

According to another embodiment, provided is a method of interlocking a lesion location between a guide image and 3D tomosynthesis image including a plurality of 3D image slices, the method including executing a program in response to generation of a pre-set trigger signal; receiving, from a second server, a guide image which is a 2D medical image of a body part, and a plurality of 3D image slices constituting 3D tomosynthesis images of the body part; and simultaneously displaying the guide image and at least one 3D image slice included in the plurality of 3D image slices, wherein a lesion location is displayed on the 3D image slice and the guide image and interlocked between the 3D image slice and the guide image.

According to another embodiment, provided is an apparatus for interlocking a lesion location between a guide image and 3D tomosynthesis images including a plurality of 3D image slices, the apparatus including a memory in which at least one program is stored; and at least one processor operated by executing the at least one program, wherein the at least one processor is configured to execute a program in response to generation of a pre-set trigger signal; receive, from a second server, a guide image which is a 2D medical image of a body part, and a plurality of 3D image slices constituting 3D tomosynthesis images of the body part, and simultaneously display the guide image and at least one 3D image slice included in the plurality of 3D image slices, and a lesion location is displayed on the 3D image slice and the guide image and interlocked between the 3D image slice and the guide image.

According to another embodiment, provided is a computer-readable recording medium having recorded thereon a program for executing the method of the first aspect or the third aspect on a computer.

Furthermore, another method, another system, and a computer-readable recording medium having recorded thereon a computer program for executing the method for implementing the present disclosure may be further provided.

Other aspects, features, and advantages will become apparent from the following drawings, claims, and detailed description of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
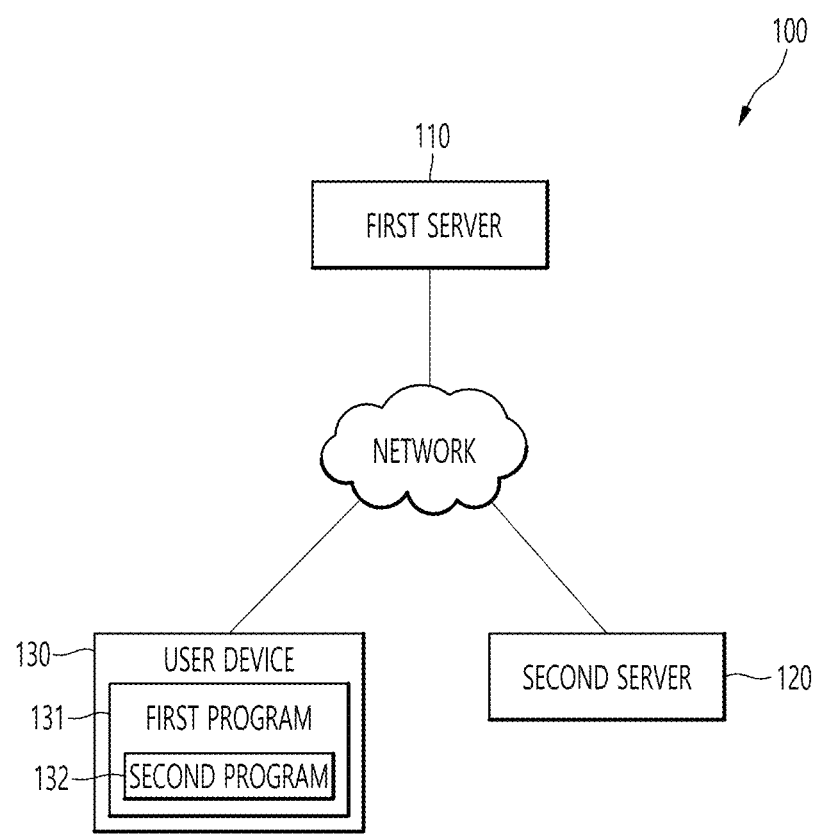
FIG. 1 is a schematic configuration diagram of a medical image checking system according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The effects and features of the present disclosure and the accompanying methods thereof will become apparent from the following description of the embodiments, taken in conjunction with the accompanying drawings. However, it should be understood that the present disclosure is not limited to the embodiments presented below, but may be implemented in various other forms and includes all transformations, equivalents, and substitutes included in the spirit and scope of the present disclosure. It should be understood, however, that the description of the embodiments is provided to enable the disclosure to be complete, and will fully convey the scope of the disclosure to one of ordinary skill in the art to which the disclosure belongs. In describing the present disclosure, when it is determined that a detailed description of a related known technology may obscure the gist of the present disclosure, the detailed description thereof will be omitted.

The terms used in the present specification are merely used to describe particular embodiments, and are not intended to limit the disclosure. An expression used in the singular encompasses the expression of the plural, unless it has a clearly different meaning in the context. In the present specification, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Some embodiments may be described in terms of functional block components and various processing steps. Such functional blocks may be realized by any number of hardware and/or software components configured to perform the specified functions. For example, the functional blocks of the disclosure may be implemented with one or more microprocessors or circuit configurations for certain functions. Also, the functional blocks of the disclosure may be implemented with any programming or scripting language. Functional blocks may be implemented in algorithms that are executed on one or more processors. Furthermore, the disclosure may employ any number of conventional techniques for electronics configuration, signal processing, and/or data processing. Terms such as "mechanism", "element", "means" and "configuration" may be used broadly and are not limited to mechanical and physical configurations.

Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

In this disclosure, the term "3D tomosynthesis images" may be interchangeably used with the term "3D image slices." The "2D medical image" and the "3D image slice" can be differentiated in a sense that they are the results of different image making methods. Specifically, 3D tomosynthesis images are the input for the AI analysis. The lesion scores and lesions markings (e.g., contour or heatmap) acquired as a result of analyzing the 3D tomosynthesis images may be projected onto a guide image for effective visualization. Here, the guide image can be a 2D medical image or one of the 3D tomosynthesis images (i.e., 3D image slice) depending on which image is available at a customer site (i.e., at a user device).

In this disclosure, the term "interlocked" is intended to mean that the AI analysis results (i.e. lesion scores, markings, etc.) derived from 3D images are the same information to be projected onto their corresponding guide image. This word can be replaced with "corresponding", "matched", or "correlated."

Hereinafter, the disclosure will be described in detail with reference to accompanying drawings.

FIG. 1 is a schematic configuration diagram of a medical image checking system according to an embodiment.

A medical image checking system 100 includes a first server 110, a second server 120, and a user device 130.

Examples of the user device 130 may include a smart phone, a tablet PC, a PC, a smart TV, a mobile phone, a personal digital assistant (PDA), a laptop computer, a media player, a micro server, a global positioning system (GPS) device, an e-book terminal, a digital broadcasting terminal, a navigation device, a kiosk, an MP3 player, a digital camera, home appliance, a camera-equipped device, and other mobile or non-mobile computing devices, but are not limited thereto. Also, the user device 130 may be a wearable device such as a wristwatch, glasses, a hair band, and a ring having a communication function and a data processing function. However, embodiments are not limited thereto.

The first server 110 refers to a server that integrally processes functions for storing, reading, and navigating medical image information. For example, the first server 110 may be a picture archiving and communication system (PACS) server, but is not limited thereto. The first server 110 may convert radiographic images obtained through X-ray, computed tomography (CT), positron emission tomography (PET), single photon emission computed tomograph (SPECT), etc., ultrasound images, and magnetic resonance imaging (MRI) images into digital images and stores the digital images in a large-capacity storage device simultaneously as the digital images are obtained, and thus a user may read the digital images through a monitor. Here, the user may refer to a radiologist or a radiology specialist, but is not limited thereto, and may include a person who makes a medical judgment or diagnosis by reading medical images.

The first server 110 may store and manage images according to a certain standard. For example, the first server 110 may store and manage images according to the digital imaging and communications in medicine (DICOM) standard.

Meanwhile, a first program 131 installed on the user device 130 may be a program associated with the first server 110. The user device 130 may be connected to the first server 110 through the first program 131 and transmit/receive data. A user of the user device 130 may read an image through the first program 131 and diagnose the condition of a patient. For example, the first program 131 may be a picture archiving and communication system (PACS) viewer program, but is not limited thereto.

The second server 120 refers to a server that stores, manages, and processes data for interlocking lesion locations between a guide image and three dimensional (3D) tomosynthesis images including a plurality of 3D image slices.

The second server 120 may receive a medical image set corresponding to at least one patient from the first server 110. The medical image set may include 3D tomosynthesis images including a plurality of 3D image slices and a guide image corresponding to the 3D tomosynthesis images. The guide image may be a two dimensional (2D) medical image (e.g., combo 2D, Synthetic 2D) or a certain 3D image slice (e.g., a 3D image slice with the highest lesion score calculated through an artificial intelligence model), but is not limited thereto. The lesion score may refer to the AI's confidence score of the lesion being malignant as its interpretation result of 3D image slices. Because how a particular lesion is displayed throughout different 3D image slices may look slightly different according to the AI's perspective, the lesion score of the same lesion can vary from slice to slice.

The second server 120 may obtain one or more pieces of lesion information by analyzing a medical image set received from the first server 110 by using an artificial intelligence model. For example, the second server 120 may predict the location of a lesion and a lesion score on the guide image and the 3D image slices by using an artificial intelligence model.

Meanwhile, a second program 132 installed in the user device 130 may be a program associated with the second server 120. The user device 130 may be connected to the second server 120 through the second program 132 and transmit/receive data. The user device 130 may invoke the second program 132 when a certain condition is satisfied.

According to an embodiment, the user device 130 may invoke the second program 132 in response to generation of a pre-set trigger signal while the first program 131 is being executed. A pre-set trigger signal may be generated when a shortcut key or a button on the user device 130 is pressed. For example, the second program 132 may be a viewer program and may be installed in the first program 131 as an in-app program.

After the second program 132 is invoked, the user device 130 may receive data by communicating with the second server 120 through the second program 132. The user device 130 may receive a guide image in which lesion information is displayed and a plurality of 3D image slices from the second server 120 through the second program 132. The second program 132 may configure a user interface (UI), such that a guide image and a plurality of 3D image slices are simultaneously displayed. Also, the second program 132 may configure the UI, such that a guide image and a plurality of 3D image slices are displayed in parallel. A detailed method of displaying a guide image and a plurality of 3D image slices will be described later.

The user device 130, the first server 110, and the second server 120 may perform communication by using a network. For example, a network includes a local area network (LAN), a wide area network (WAN), a value added network (VAN), a mobile radio communication network, a satellite communication network, and combinations thereof, is a data communication network in a comprehensive sense that enables the network constituent entities shown in FIG. 1 to communicate smoothly with one another, and may include a wired Internet, a wireless Internet, and a mobile wireless communication network. Also, examples of a wireless communication may include, but is not limited to, wireless LAN (Wi-Fi), Bluetooth, Bluetooth low energy, Zigbee, Wi-Fi Direct (WFD), ultra wideband (UWB), infrared communication (infrared Data Association (IrDA)), and Near Field Communication (NFC).

Figure 2:
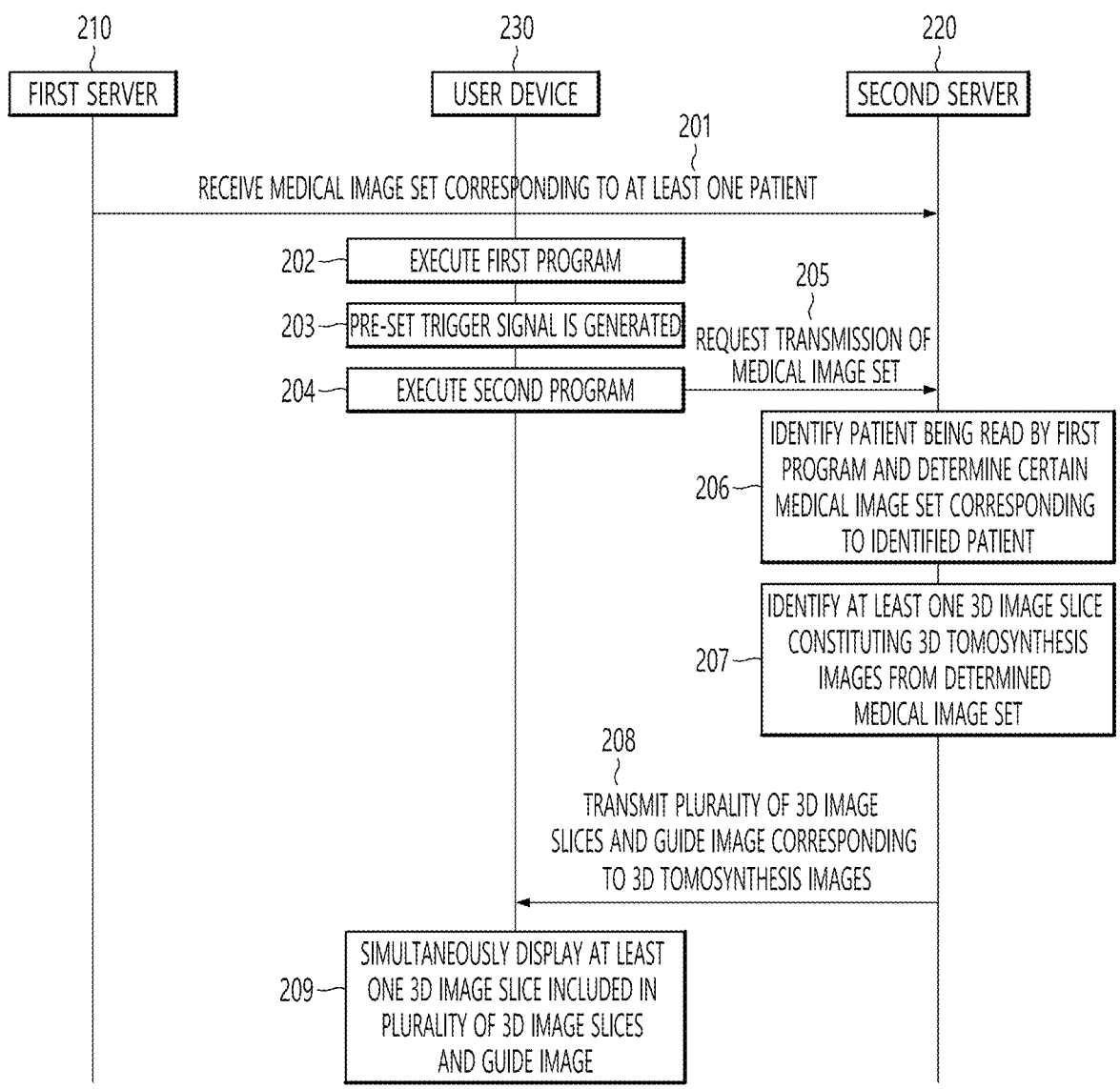
FIG. 2 is a flowchart illustrating operations of a server and an apparatus according to an embodiment.

FIG. 2 is a flowchart illustrating operations of a server and an apparatus according to an embodiment.

Referring to FIG. 2, a first server 210, a second server 220, and a user device 230 may correspond to the first server 110, the second server 120, and the user device 130 of FIG. 1, respectively.

In operation 201, the second server 220 may receive a medical image set corresponding to at least one patient from the first server 210. The first server 210 stores medical image sets for a plurality of patients, and the second server 220 may receive a medical image set from the first server 210 when a certain condition is satisfied and update the corresponding medical image set previously stored in the second server 220. The certain condition may include a pre-set period, a user's request signal, etc.

According to an embodiment, the second server 220 may further receive medical images obtained by an external medical imaging device. The second server 220 may further receive the medical images, in addition to medical image sets, from the first server 210 and other external devices. The external medical imaging device may refer to a medical imaging device of a different type from that of a medical imaging device that obtained a guide image and a plurality of 3D image slices included in a medical image set.

Alternatively, the external medical imaging device may correspond to a medical imaging device of the same type as the medical imaging device that obtained a guide image and a plurality of 3D image slices included in a medical image set, and the second server 220 may further include medical images obtained at a different time than when the medical images included in the medical image set are obtained. For example, the external medical imaging device may include an X-ray device, a magnetic resonance imaging (MRI) device, a computed tomography (CT) device, and an ultra sound (US) device.

In operation 202, the user device 230 may execute a first program. A user using the user device 230 may execute a first program to store, read, and navigate medical image information.

In operation 203, a pre-set trigger signal may be generated in the user device 230. A pre-set trigger signal may be generated as an input of pressing a shortcut key or a button is applied to the user device 230.

In operation 204, in response to the generation of the pre-set trigger signal, the user device 230 may execute a second program. According to an embodiment, the user device 230 may execute the second program 132 in response to generation of a pre-set trigger signal while the first program 131 is being executed.

In operation 205, the second program may communicate with the second server 220 and request the second server 220 to transmit a medical image set.

In operation 206, the second server 220 may identify a patient being read by the first program and determine a certain medical image set corresponding to an identified patient. For example, when the second program is executed and a request signal is transmitted to the second server 220 while medical image information regarding a patient A is being checked in the first program, the second server 220 may determine a certain medical image set corresponding to the patient A. The medical image set may include 3D tomosynthesis images including a plurality of 3D image slices and a guide image corresponding thereto. The guide image may be a 2D medical image. The request sent in operation 205 may include information, such as an identifier of the patient A or an identifier of the 3D image slice, indicating what medical information was being read by the first program when the pre-set trigger signal is generated in operation 203. Accordingly, the second server 220 may identify the patient A or a particular 3D image slice being processed by the first program from among a plurality of 3D image slices, based on the information.

According to an embodiment, the second server 220 may obtain one or more pieces of lesion information by analyzing a medical image set received from the first server 210 by using an artificial intelligence model. An analysis process may be performed when the second server 220 receives the medical image set from the first server 210 in operation 201. Alternatively, the analysis process may be performed on a certain medical image set corresponding to an identified patient after operation 206.

In operation 207, the second server 220 may identify at least one 3D image slice constituting 3D tomosynthesis images from the medical image set determined in operation 206.

Here, the at least one 3D image slice identified in operation 207 may be a first image slice from among a plurality of 3D image slices constituting 3D tomosynthesis images.

As another example, the at least one 3D image slice identified in operation 207 may be a 3D image slice being read by the first program at a time point at which a pre-set trigger signal is generated in operation 203.

As another example, the at least one 3D image slice identified in operation 207 may be a 3D image slice (hereinafter, also referred to as a focus slice) in which a particular lesion is most clearly visible from among a plurality of 3D image slices.

As another example, the focus slice may be a 3D image slice having the highest lesion score for a particular lesion based on an analysis of a medical image set by an artificial intelligence model, from among the plurality of 3D image slices.

According to embodiments, operation 207 may be performed by the user device 230.

Meanwhile, when no lesion information is confirmed as a result of analyzing a medical image set by using an artificial intelligence model, the second server 220 may identify a certain 3D image slice from among a plurality of 3D image slices. The certain 3D image slice may be a first 3D image slice from among the plurality of 3D image slices, but is not limited thereto.

In operation 208, the second server 220 may transmit a plurality of 3D image slices and a guide image corresponding to 3D tomosynthesis images to the user device 230. As aforementioned, the second server 220 may obtain one or more pieces of lesion information by analyzing a medical image set received from the first server 210 by using an artificial intelligence model, and the second server 220 may transmit the one or more pieces of lesion information to the user device 230. In detail, the second server 220 may predict the location of a lesion and a lesion score on the guide image and the 3D image slices by using an artificial intelligence model. The second server 220 may transmit the location of a lesion on the guide image and the 3D image slices and a lesion score corresponding thereto to the user device 230.

Lesion information may be displayed on a guide image and a plurality of 3D image slices transmitted from the second server 220 to the user device 230. According to an embodiment, all of the obtained lesion information may be displayed on a guide image, while only some of the obtained lesion information may be displayed on a certain 3D image slice.

In operation 209, the second program being executed on the user device 230 may simultaneously display at least one 3D image slice identified in operation 207 and a guide image. Also, the second program may configure a user interface (UI), such that a guide image and a 3D image slice are displayed in parallel. According to an embodiment, the second program may simultaneously display a guide image and a first image slice. According to another embodiment, the second program may simultaneously display a guide image and a 3D image slice being read by the first program at a time point at which a pre-set trigger signal is generated.

According to an embodiment, the second program may record feedback notes in a guide image or a 3D image slice based on a user input. Feedback notes may include markings, records, etc. made by a user on a guide image and/or a 3D image slice. The user device 230 may generate and store a separate single image by merging feedback notes in the form of an overlay on a guide image and/or a 3D image slice through the second program. Here, the single image may be implemented in the form of a Secondary Capture (SC) or a Grayscale Softcopy Presentation State (GSPS) of the DICOM format and may include implementations in various DICOM formats. Also, the user device 230 may transmit the single image to the second server 220. The second server 220 may transmit the single image to the first server 210. Also, the user device 230 may transmit the single image to the first server 210.

The second server 220 may update a medical image set by storing the single image in conjunction with a plurality of 3D image slices constituting 3D tomosynthesis images, such that the single image may be navigated together with the plurality of 3D image slices. For example, the second server 220 may update 3D tomosynthesis images by storing the single image after the last 3D image slice of the 3D tomosynthesis images. The second server 220 may provide updated 3D tomosynthesis images to be displayed, in response to generation of a pre-set trigger signal again.

The second program may receive and display an updated medical image set from the second server 220, in response to the generation of a pre-set trigger signal again.

Also, the user device 230 may display an updated medical image set through the first program. In this case, when the first program is executed, the user device 230 may display feedback notes, which are recorded through the second program, without separately executing the second program.

According to an embodiment, the first server 210 and the second server 220 may be integrated so that a single server performs the functions of the first server 210 and the second server 220 described above. According to another embodiment, the second server 220 may be integrated into the user device 230 so that the user device 230 performs the functions of the second server 220 described above.

Figure 3:
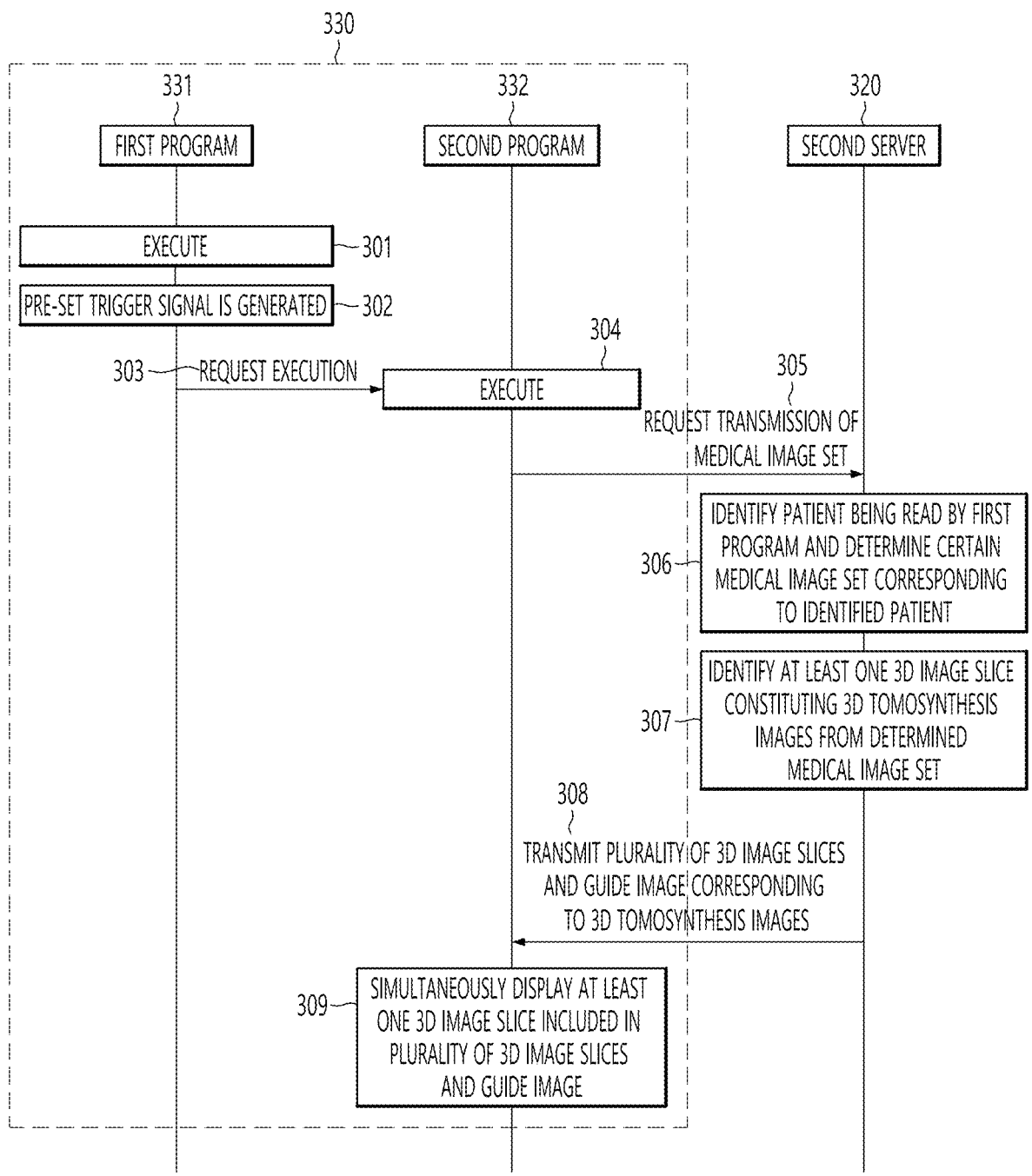
FIG. 3 is a flowchart illustrating operations of programs executed on a device and operations of a server according to an embodiment.

FIG. 3 is a flowchart illustrating operations of programs executed on a device and operations of a server according to an embodiment.

Referring to FIG. 3, a second server 320 and a user device 330 may correspond to the second server 120 and the user device 130 of FIG. 1, respectively. Meanwhile, a first program 331 and a second program 332 may be installed and executed on the user device 330.

The first program 331 may be a program associated with a first server (not shown). A user of the user device 330 may read an image through the first program 331 and diagnose the condition of a patient. For example, the first program 331 may be a PACS viewer program, but is not limited thereto.

The second program 332 may be a program associated with the second server 320. For example, the second program 332 may be a viewer program and may be installed in the first program 331 as an in-app program.

In operation 301, the first program 331 installed on the user device 330 may be executed. A user using the user device 330 may execute the first program 331 to store, read, and navigate medical image information.

In operation 302, a pre-set trigger signal may be generated while the first program 331 is being executed. The first program 331 may determine that a pre-set trigger signal has been generated by recognizing an input of pressing a short-cut key or a button.

In operation 303, the first program 331 may transmit an execution request for executing the second program 332 to the second program 332 in response to the generation of the pre-set trigger signal.

In operation 304, in response to reception of the execution request from the first program 331, the second program 332 installed on the user device 330 may be executed.

Operations 305 to 309 of FIG. 3 may correspond to operations 205 to 209 of FIG. 2, respectively.

In operation 305, the second program 332 may request the second server 320 to transmit a medical image set.

In operation 306, the second server 320 may identify a patient being read by the first program 331 and determine a certain medical image set corresponding to an identified patient.

In operation 307, the second server 320 may identify at least one 3D image slice constituting 3D tomosynthesis images from the medical image set determined in operation 306.

In operation 308, the second server 320 may transmit a plurality of 3D image slices and a guide image corresponding to 3D tomosynthesis images to the user device 330.

Also, the second server 320 may obtain one or more pieces of lesion information by analyzing a medical image set received from the first server (not shown) by using an artificial intelligence model. The second server 320 may transmit one or more pieces of lesion information obtained together with a plurality of 3D image slices and a guide image associated with the plurality of 3D image slices to the user device 330. In detail, the second server 320 may predict the location of a lesion and a lesion score on the guide image and the 3D image slices by using an artificial intelligence model. The second server 320 may transmit the location of a lesion on the guide image and the 3D image slices and a lesion score corresponding thereto to the user device 330.

In operation 309, the second program 332 may simultaneously display at least one 3D image slice included in a plurality of 3D image slices and a guide image.

Figure 4:
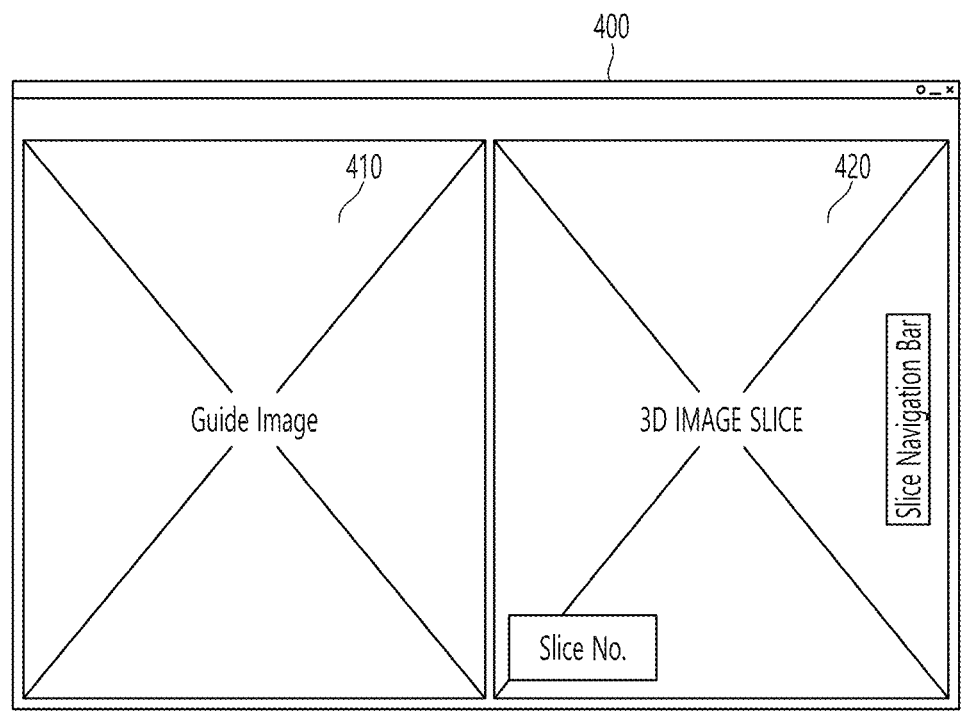
FIG. 4 is a diagram illustrating an example of a screen image displayed in second program, according to an embodiment.

FIG. 4 is a diagram illustrating an example of a screen image displayed when a second program is executed, according to an embodiment.

Referring to FIG. 4, a screen image 400 displayed when a user device executes a second program is shown.

The second program may receive, from a second server, 3D tomosynthesis images and a guide image, which are matched to each patient. The 3D tomosynthesis images may include a plurality of 3D image slices. The guide image may be a 2D medical image (e.g., combo 2D, Synthetic 2D) or a certain 3D image slice (e.g., a 3D image slice with the highest lesion score calculated through an artificial intelligence model), but is not limited thereto.

The second program may simultaneously display a guide image and 3D tomosynthesis images on the screen image 400. Referring to FIG. 4, a UI may be configured, such that a guide image is displayed in a left region 410 of the screen image 400 and 3D tomosynthesis images are displayed in a right region 420.

Meanwhile, since 3D tomosynthesis images include a plurality of 3D image slices, any one 3D image slice from among the plurality of 3D image slices may be displayed in the right region 420.

The second program may configure the UI to display a slice number (Slice No.) of a 3D image slice and a slice navigation tool in the right region 420. The second program may perform navigation for 3D tomosynthesis images in the depth-wise direction through the slice navigation tool. The second program may display any one 3D image slice from among the plurality of 3D image slices based on a user input to the slice navigation tool. Description of the slice navigation tool will be given later with reference to FIG. 7.

Meanwhile, in the following drawings, for convenience of explanation, a 2D mammography image is used as an example of a guide image, and 3D breast tomosynthesis images are used as an example of 3D tomosynthesis images. However, the present disclosure is not limited to images obtained by photographing the breast and may be equally applied to other body parts such as the chest.

Figure 5:
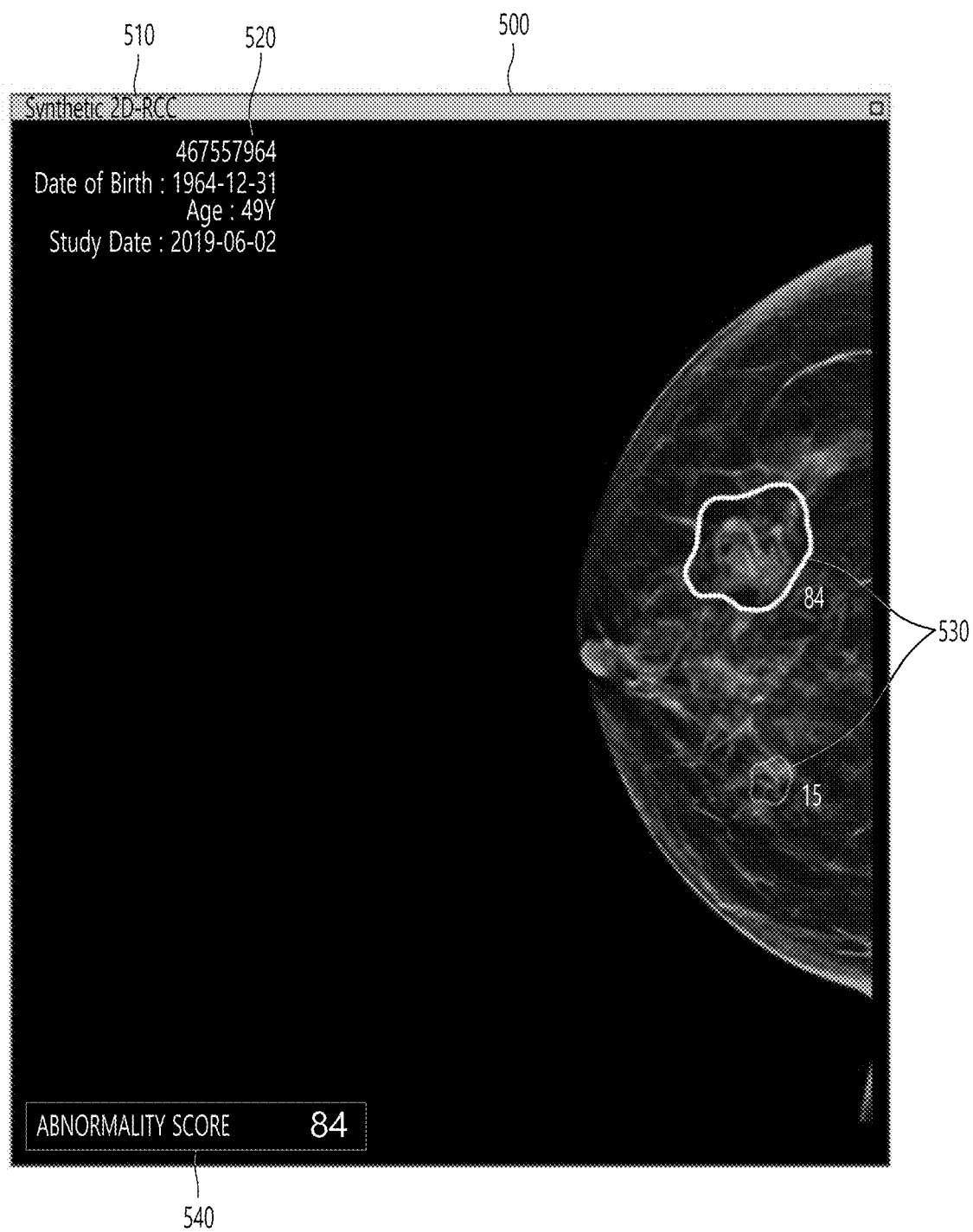
FIG. 5 is a diagram illustrating an example of a screen image in which a guide image is displayed, according to an embodiment.

FIG. 5 is a diagram illustrating an example of a screen image in which a guide image is displayed, according to an embodiment.

Referring to FIG. 5, a screen image 500 in which a guide image is displayed is shown.

A second program may display a title 510 of the guide image in the screen image 500. The second program may provide various types of guide images and may display the title 510 corresponding to the type of a provided guide image. For example, the second program may display "combo 2D", "synthetic 2D" and "3D image slice corresponding to the highest lesion score" as the title 510 according to the type of a guide image.

Also, the second program may display patient information 520 in the screen image 500. The patient information 520 may include, but is not limited to, a patient identification number, date of birth, an age, and an examination date.

Also, the second program may display one or more pieces of lesion information 530 on a guide image. As described above with reference to FIG. 1, a second server that communicates with the second program may obtain one or more pieces of lesion information by analyzing a medical image set received from a first server by using an artificial intelligence model. In detail, the second server may predict the location of a lesion and a lesion score on the guide image and the 3D image slices by using an artificial intelligence model. Based on lesion information received from the second server, the second program may display the location and a score for each of all lesions on the guide image.

Also, the second program may display an abnormality score 540 in the screen image 500. For example, the highest lesion score from among lesion scores for a plurality of lesions displayed on the guide image may be the abnormality score 540. Referring to FIG. 5, since respective lesion scores for two detected lesions are 84 points and 15 points, the second program may determine that the 84 points, which is the highest point, is the abnormality score 540 and display the abnormality score 540 in the screen image 500.

Figure 6:
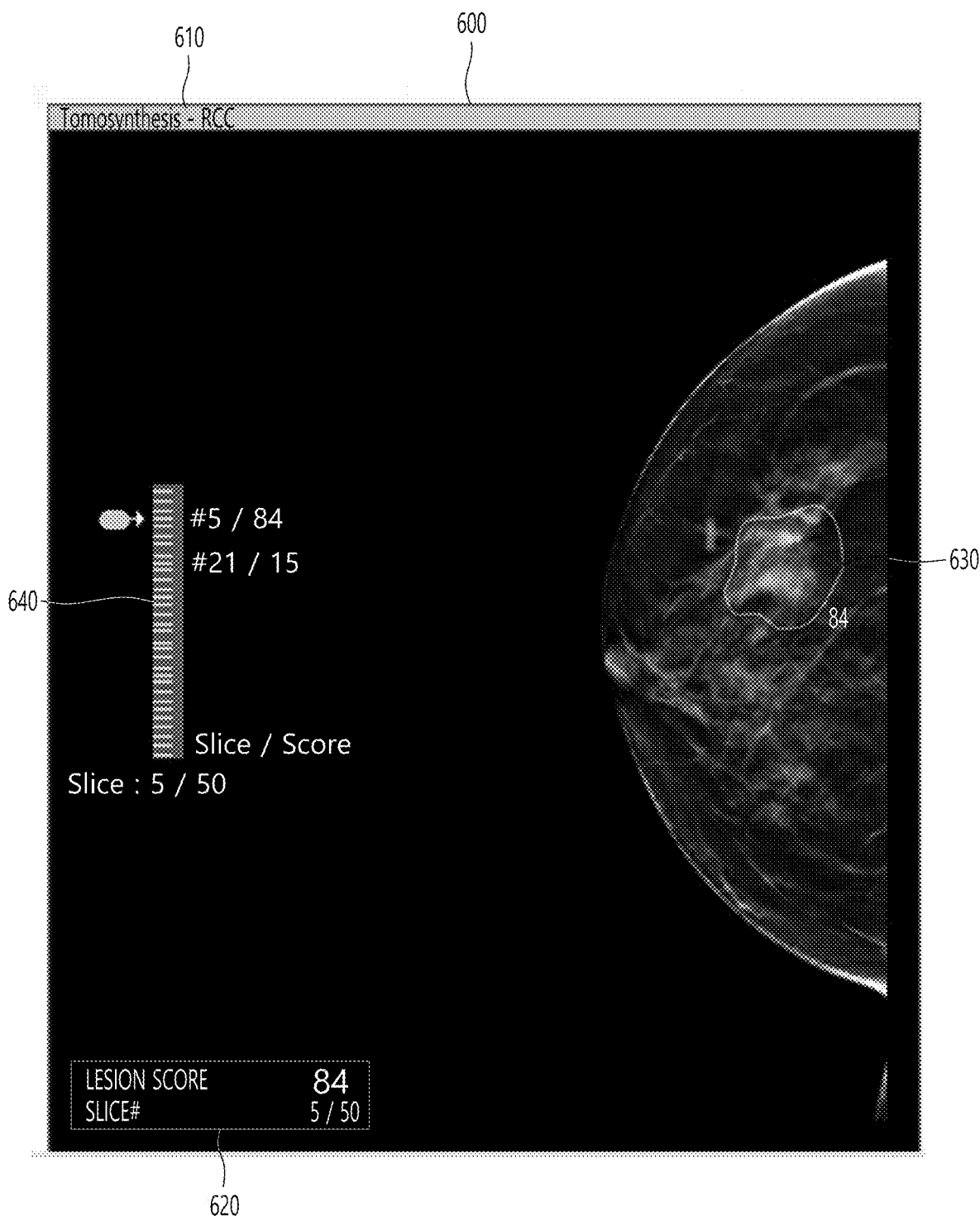
FIG. 6 is a diagram illustrating an example of a screen image in which a three dimensional (3D) image slice is displayed, according to an embodiment.

FIG. 6 is a diagram illustrating an example of a screen image in which a 3D image slice is displayed, according to an embodiment.

Referring to FIG. 6, a screen image 600 in which a certain 3D image slice is displayed is shown.

A second program may display a title 610 of a 3D image slice in the screen image 600. For example, the second program may display "tomosynthesis" as the title 610.

Also, the second program may display slice information 620 in the screen image 600. The slice information 620 may include a slice number and a lesion score. In detail, since 3D tomosynthesis images include a plurality of 3D image slices, a slice number indicating the number of a 3D image slice currently displayed in the screen image 600 from among the plurality of 3D image slices may be displayed in the screen image 600. Also, the lesion score of the corresponding 3D image slice may be displayed together in the screen image 600.

Also, the second program may display one or more pieces of lesion information 630 on a guide image. While the second program displays all lesion information on a guide image in FIG. 5, the second program may display only some of lesion information on a certain 3D image slice in FIG. 6.

Referring to FIG. 6, it may be seen that a 3D image slice currently being displayed in the screen image 600 is a fifth slice from among a total of fifty 3D image slices, and the fifth slice includes a lesion having a lesion score of 84 points.

Also, the second program may display a slice navigation tool 640 in the screen image 600. The second program may perform navigation for 3D tomosynthesis images in the depth-wise direction through the slice navigation tool 640. The slice navigation tool 640 may include, but is not limited to, a slider bar, a slider handle, and a slice number/lesion score.

Figure 7:
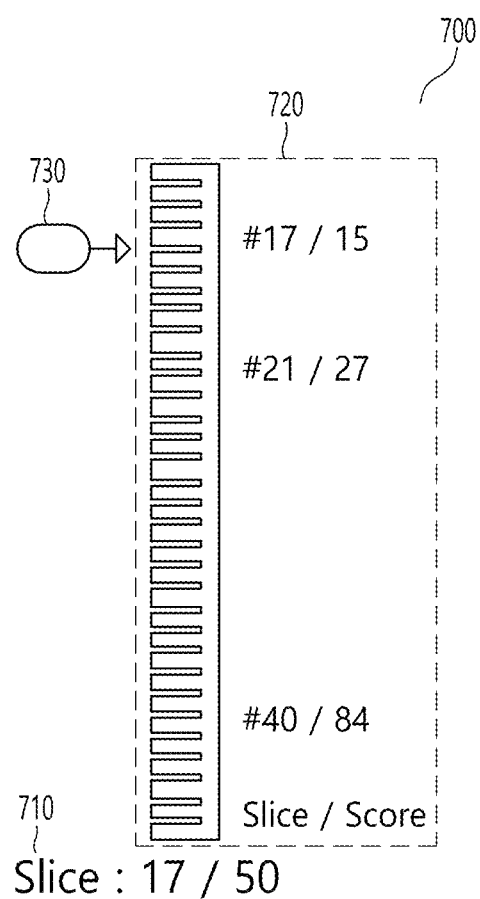
FIG. 7 is a diagram illustrating an example of functions of a slice navigation tool according to an embodiment.

FIG. 7 is a diagram illustrating an example of functions of a slice navigation tool according to an embodiment.

The 3D tomosynthesis images include a plurality of 3D image slices, and a slice navigation tool 700 may be used to move to a 3D image slice desired by a user.

The second program may perform navigation for 3D tomosynthesis images in the depth-wise direction through the slice navigation tool 700. The second program may display any one 3D image slice from among the plurality of 3D image slices based on a user input to the slice navigation tool 700.

Referring to FIG. 7, the slice navigation tool 700 may include a slice number 710, a slider bar 720, and a slider handle 730, but the elements included in the slice navigation tool 700 are not limited thereto.

The slice number 710 may include the total number of 3D image slices constituting 3D tomosynthesis images and the number of a 3D image slice currently being displayed in a screen image. Referring to FIG. 7, it may be seen that there are a total of fifty 3D image slices constituting 3D tomosynthesis images, and a 3D image slice currently being displayed in the screen image corresponds to the 17th 3D image slice.

The slider bar 720 includes an indicator corresponding to each of the plurality of 3D image slices. The slider bar 720 may display as many indicators as the number of 3D image slices. FIG. 7 shows indicators in the form of a grid, and, since the number of 3D image slices is 50, it may be seen that fifty indicators are displayed.

Also, information regarding a focus slice may be displayed on the slider bar 720. The focus slice refers to at least one 3D image slice in which a particular lesion is most clearly visible from among a plurality of 3D image slices. The slice number of the focus slice and the lesion score of a lesion included in the focus slice may be displayed on the slider bar 720 as focus slice information. Referring to FIG. 7, it may be seen that the lesion score of a lesion included in the 17th 3D image slice is 15 points, the lesion score of a lesion included in the 21st 3D image slice is 27 points, and the lesion score of a lesion included in the 40th slice is 84 points.

According to an embodiment, when an input for selecting any one of at least one piece of focus slice displayed on the slider bar 720 is received, the second program may display a corresponding focus slice in the screen image 600. For example, when a user clicks '#21/27', the second program may display the 21st 3D image slice in the screen image 600.

The slider handle 730 may be displayed at a position adjacent to the slider bar 720 to indicate a 3D image slice currently being displayed. The slider handle 730 may be positioned at an indicator corresponding to a 3D image slice currently being displayed. A user may navigate 3D tomosynthesis images in the depth-wise direction by using the slider handle 730. For example, the user may select a 3D image slice to check, through a clicking action and a dragging action on the slider handle 730. The second program may provide a selected 3D image slice to the user in real time.

FIGS. 8A to 8D are diagrams illustrating an example of a method of interlocking lesion locations between a guide image and a plurality of 3D image slices, according to an embodiment.

Referring to FIGS. 8A to 8D, a guide image is shown in a left region 810 of a screen image 800, and a 3D image slice is shown in a right region 820 of the screen image 800.

Figure 8A:
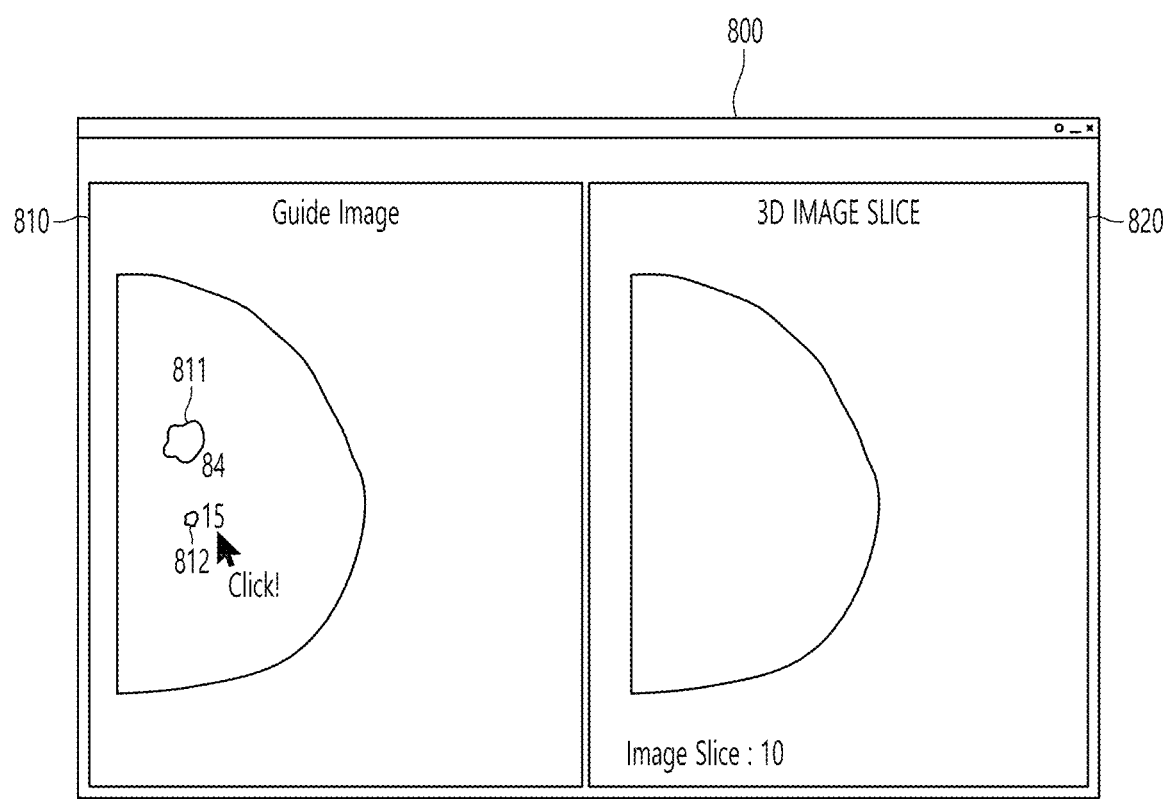
FIGS. 8A to 8D are diagrams illustrating an example of a method of interlocking lesion locations between a guide image and a plurality of 3D image slices, according to an embodiment.

Referring to FIG. 8A, a plurality of pieces of lesion information 811 and 812 may be displayed on the guide image. In detail, a position, a shape, and a lesion score (84 points) of first lesion information 811 and a position, a shape, and a lesion score (15 points) of second lesion information 812 may be displayed on the guide image. In this case, the 3D image slice displayed in the right region 820 may be any 3D image slice. In the right region 820, the slice number of a currently displayed 3D image slice may be displayed together in the screen image 800.

Meanwhile, the 3D image slice displayed in the right region 820 may be changed in response to an input for selecting any one of the plurality of pieces of lesion information 811 and 812. The second program may display a 3D image slice corresponding to the highest lesion score of lesion information from among the plurality of 3D image slices in the right region 820.

Figure 8B:
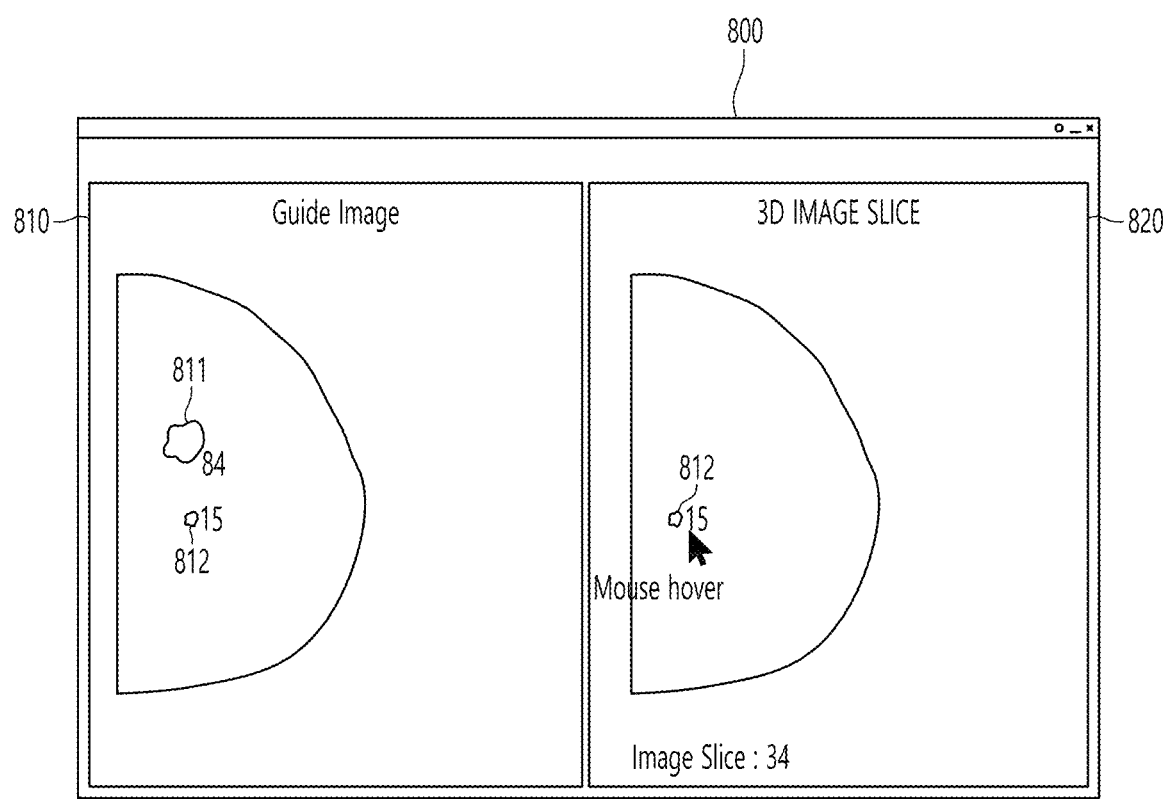

Referring to FIG. 8B, in response to an input for selecting the second lesion information 812, the second program may display a 3D image slice corresponding to the highest lesion score of the second lesion information 812 in the right region 820. In other words, although the 10th 3D image slice is displayed in the right region 820 in FIG. 8A, it may be seen that the 34th 3D image slice is displayed in the right region 820 in FIG. 8B after the second lesion information 812 in the guide image is selected. The second lesion information 812 may be displayed together with the 3D image slice displayed in the right region 820.

Figure 8C:
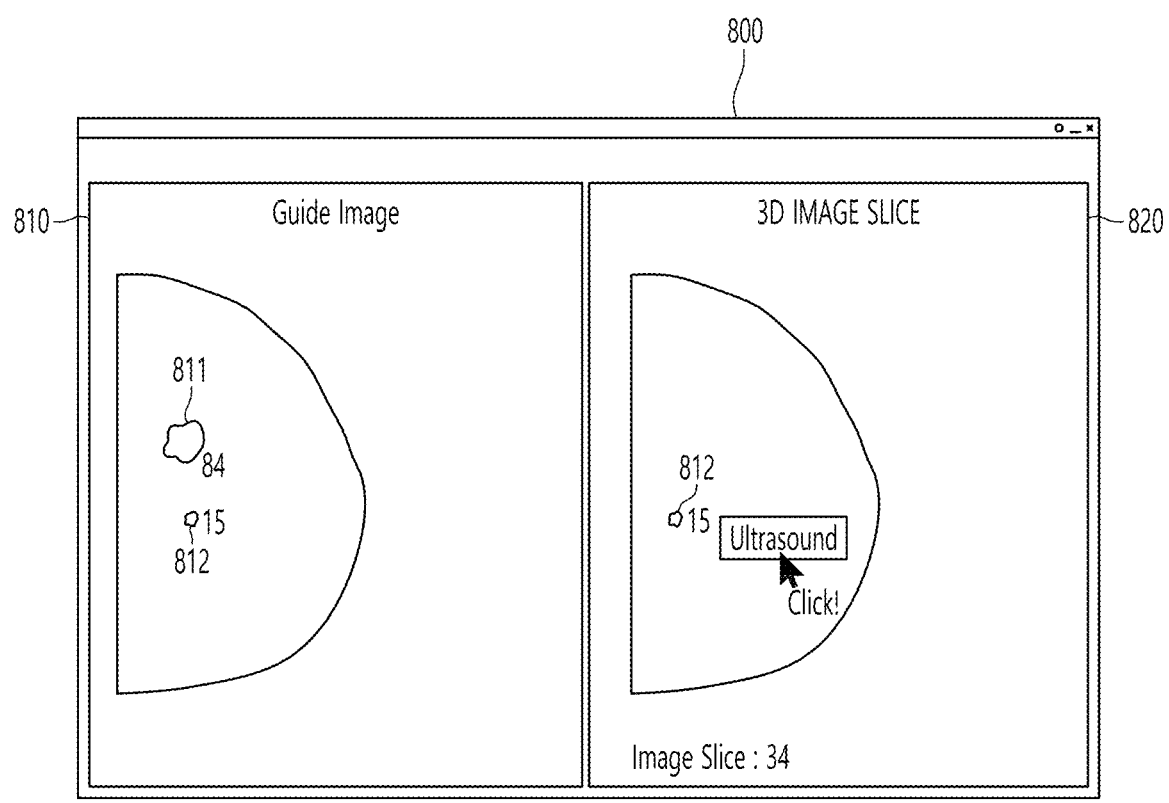

Referring to FIG. 8C, the second program may indicate whether a medical image related to the lesion information displayed on the 3D image slice in the right region 820 exists. The second program may receive images obtained by an external medical imaging device from the second server. When a medical image obtained by an external medical imaging device exists, the second program may display the medical image obtained by the external medical imaging device in response to selection of lesion information displayed in the right region 820. The external medical imaging device may include an MRI device, a CT device, and an ultrasound imaging device. It may be seen in FIG. 8C that an ultrasound image exists as a medical image related to the second lesion information 812 displayed in the right region 820.

Figure 8D:
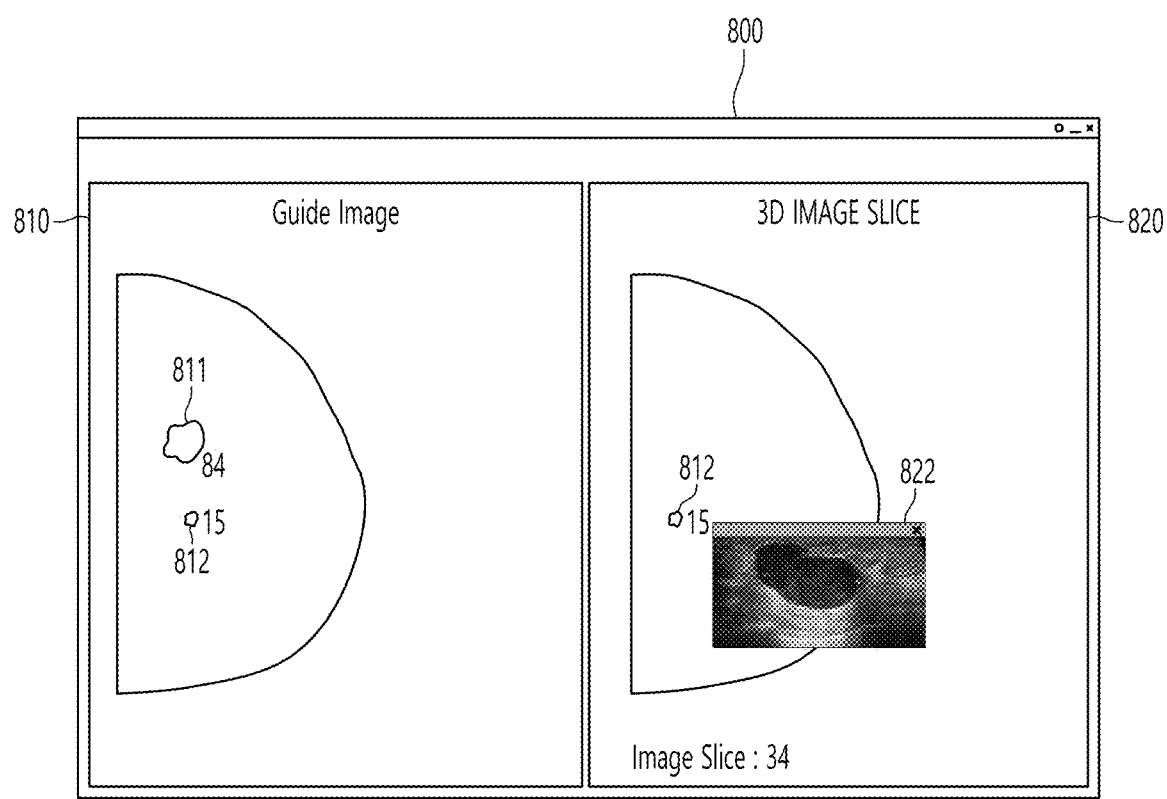

Referring to FIG. 8D, the second program may display a pre-stored medical image 822 in response to an input of selecting the second lesion information 812 displayed in the right region 820. For example, the second program may display a pre-stored medical image through a separate sub window to display the pre-stored medical image together with a 3D image slice.

According to an embodiment, the second program may process a medical image obtained by an external medical imaging device to correspond to depth information of a currently displayed 3D image slice and position information of a lesion displayed on the 3D image slice. To this end, the second program may obtain photographing location information at the time of taking the medical image. In detail, the second program may compare and analyze depth information of a 3D image slice and position information of a lesion with photographing location information of a medical image. The second program may extract and display only a region corresponding to the depth information of the 3D image slice and position information of the lesion from among regions of the medical image based on a result of the analysis.

Figure 9:
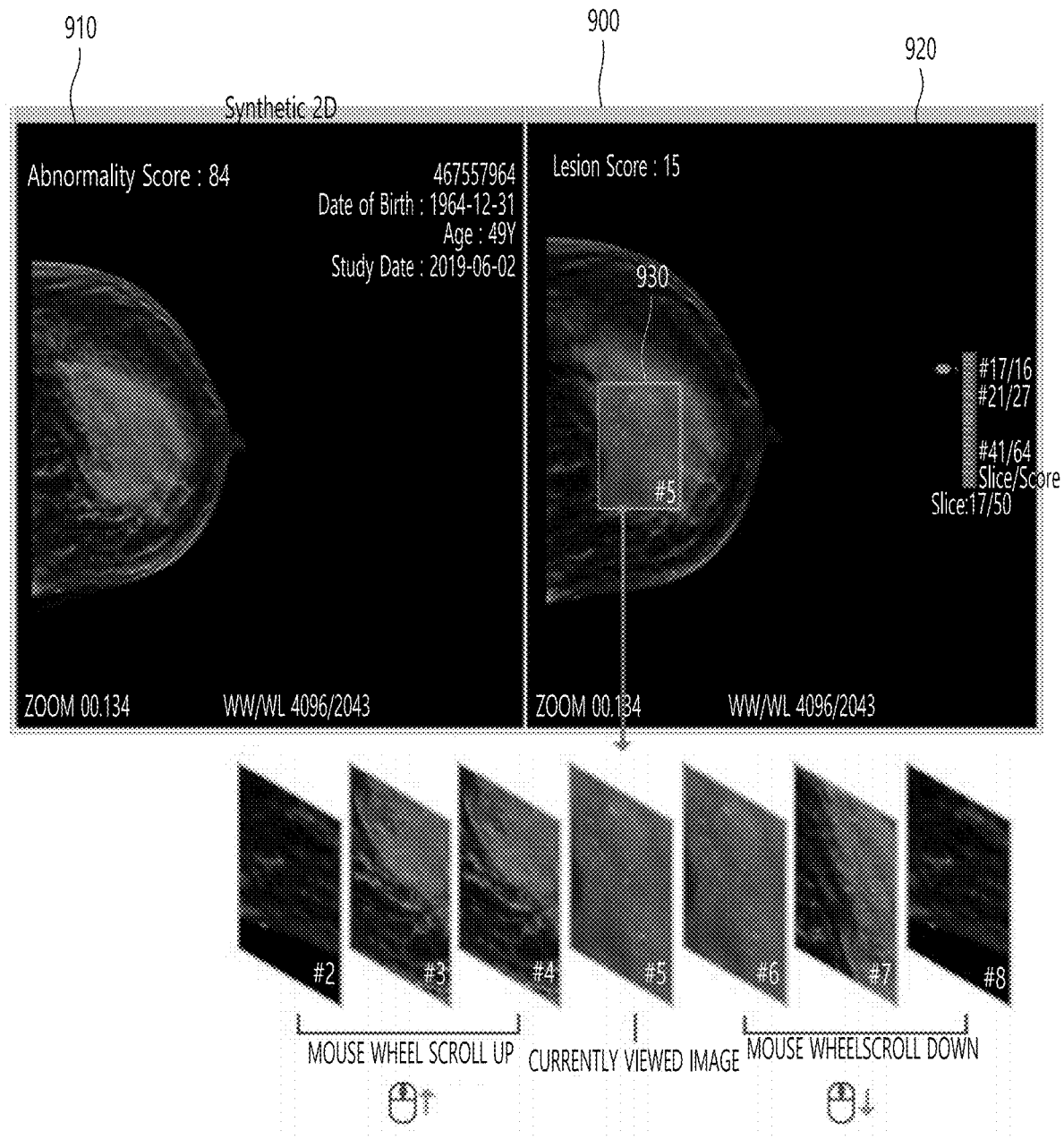
FIG. 9 is a diagram illustrating an example of a method of navigating a 3D image slice, according to an embodiment.

FIG. 9 is a diagram illustrating an example of a method of navigating a 3D image slice, according to an embodiment.

Referring to FIG. 9, a guide image is shown in a left region 910 of a screen image 900, and a 3D image slice is shown in a right region 920 of the screen image 900.

According to an embodiment, the second program may set a partial region of a 3D image slice displayed in the right region 920 as an enlarged region 930. For example, when a user hovers a mouse pointer over a 3D image slice in a state in which an enlargement function is executed, a region corresponding to a hovered position may be set as the enlarged region 930. The position, the size, and the shape of the enlarged region 930 may be variously set according to user settings. The enlarged region 930 may be displayed as a separate window or displayed as an overlay on a designated region on the 3D image slice.

In response to a user input being received, the second program may change the 3D image slice displayed in the enlarged region 930. Also, even if the enlarged region 930 is changed, the second program may maintain a previous 3D image slice in the remaining regions other than the enlarged region. The user input includes, but is not limited to, mouse wheel scrolling.

In detail, assume that a mouse wheel scrolling input for the enlarged region 930 is received while the enlarged region 930 is shown in a 3D image slice currently being displayed in the right region 920 (hereinafter, referred to as a reference slice). The second program may change the 3D image slice displayed in the enlarged region 930, such that a 3D image slice immediately before or after the reference slice is displayed according to a scrolling direction while the reference slice image is displayed in the remaining regions other than the enlarged region 930. For example, when the reference slice is the fifth 3D image slice, even when another 3D image slice is displayed in the enlarged region 930, the fifth 3D image slice may be maintained and displayed in regions other than the enlarged region 930.

Meanwhile, a slice number indicating the number of a currently displayed 3D image slice may be displayed together in the enlarged region 930.

In the present disclosure, it is possible to conveniently check 3D image slices adjacent to a region set as the enlarged region 930, thereby improving the efficiency of image reading and the accuracy of diagnosis.

Figure 10:
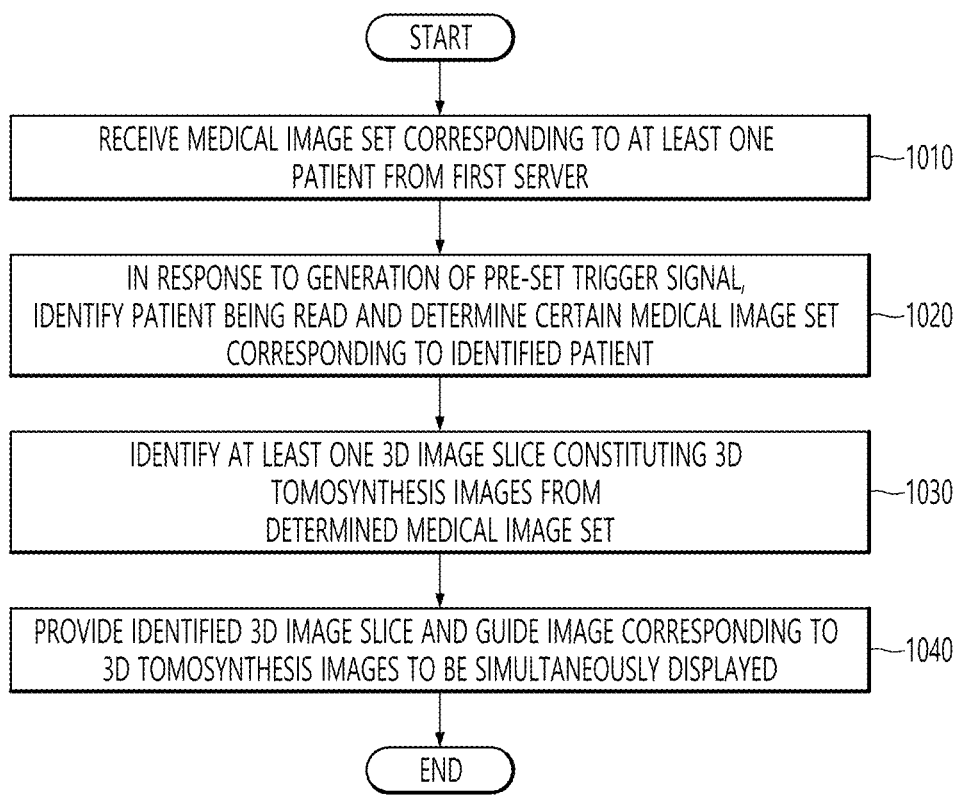
FIG. 10 is a flowchart of a method of operating a server for interlocking a lesion location between a guide image and 3D tomosynthesis images including a plurality of 3D image slices, according to an embodiment.

FIG. 10 is a flowchart of a method of operating a server for interlocking a lesion location between a guide image and 3D tomosynthesis images including a plurality of 3D image slices, according to an embodiment.

Referring to FIG. 10, in operation 1010, a server (e.g., second sever 220 of FIG. 2) may receive a medical image set corresponding to at least one patient from an external server (e.g., first server 210 of FIG. 2). As aforementioned, the first server 210 and the second server 220 may be integrated into a single server. Also, the second server 220 may be integrated into the user device 230.

Also, the server may receive a medical image obtained by an external medical imaging device.

In operation 1020, the server may identify a patient being read in response to generation of a pre-set trigger signal and may determine a certain medical image set corresponding to the identified patient.

In operation 1030, the server may identify at least one 3D image slice constituting 3D tomosynthesis images from among a plurality of medical images included in the certain medical image set.

In operation 1040, the server may provide the identified 3D image slice and a guide image corresponding to the 3D tomosynthesis images to a user device to be simultaneously displayed.

The server may obtain one or more pieces of lesion information obtained by analyzing the certain medical image set by using an artificial intelligence model.

All of the obtained lesion information may be displayed on the guide image, while only a part of the obtained lesion information corresponding to the identified 3D image slice from among the one or more pieces of lesion information may be displayed on the identified 3D image slice.

That is, if a plurality of pieces of lesion information are obtained from the certain medical image set, all of the plurality of pieces of lesion information may be displayed on the guide image, and some of the plurality of pieces of lesion information may be displayed on the identified 3D image slice.

Coordinate information of a region in which some of lesion information is displayed on the identified 3D image slice and coordinate information of a region in which of the same lesion information is displayed on the guide image may be set to correspond to each other.

The server may provide a slice navigation tool to be displayed on a display region of the identified 3D image slice such that a user may navigate 3D tomosynthesis images in the depth-wise direction by using the slice navigation tool.

According to an embodiment, the slice navigation tool may include an indicator for identifying each of the plurality of 3D image slices. Also, for each of a plurality of pieces of lesion information displayed on the guide image, identification information of a focus slice and a lesion score for the corresponding lesion may be displayed at a position corresponding to the indicator of the focus slice.

The server may receive a separate single image obtained by merging an identified 3D image slice with feedback notes recorded in the identified 3D image. Also, the server may receive a separate single image obtained by merging a guide image slice with feedback notes recorded in guide image.

The server may update 3D tomosynthesis images by storing the single image in conjunction with the plurality of 3D image slices constituting 3D tomosynthesis images, such that the single image may be navigated together with the plurality of 3D image slices. The server may provide updated 3D tomosynthesis images to be displayed, in response to generation of a pre-set trigger signal again.

Also, a user device may display an updated medical image set through the first program. In this case, when the first program is executed, the user device may display feedback notes, which are recorded through the second program, without separately executing the second program.

Figure 11:
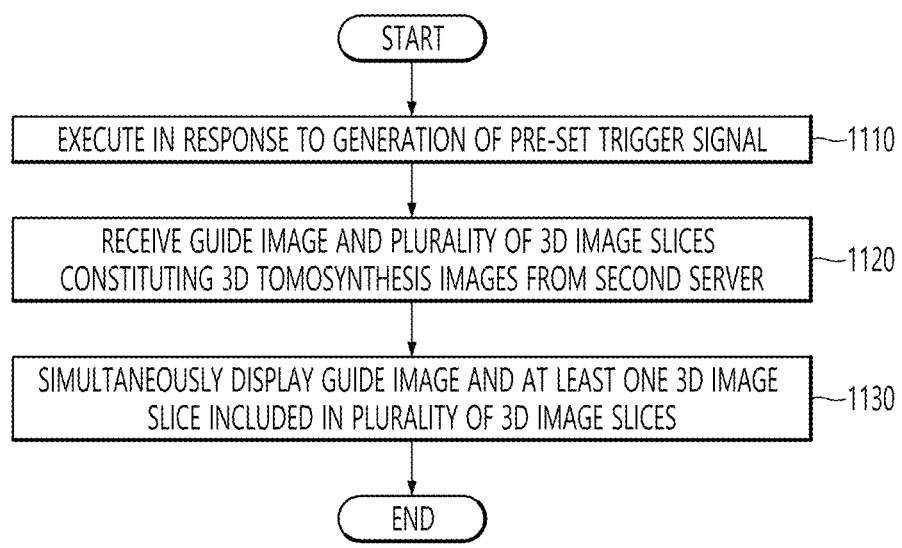
FIG. 11 is a flowchart of a method of operating a program for interlocking a lesion location between a guide image and 3D tomosynthesis images including a plurality of 3D image slices, according to an embodiment.

FIG. 11 is a flowchart of a method of operating a program for interlocking a lesion location between a guide image and 3D tomosynthesis images including a plurality of 3D image slices, according to an embodiment. The method shown in FIG. 11 may be performed by a user device 230 of FIG. 2.

Referring to FIG. 11, in operation 1110, a program may be executed in response to generation of a pre-set trigger signal.

In operation 1120, the program may receive a guide image and a plurality of 3D image slices constituting 3D tomosynthesis images from a second server.

The guide image may correspond to a 2D medical image.

In operation 1130, the program may simultaneously display the guide image and at least one 3D image slice included in the plurality of 3D image slices.

The program may identify at least one 3D image slice from among the plurality of 3D image slices. When there are a plurality of pieces of lesion information, all of the plurality of pieces of lesion information may be displayed on the guide image, and some of the plurality of pieces of lesion information may be displayed on the identified 3D image slice.

The coordinate information of a region in which some of lesion information is displayed on the identified 3D image slice and coordinate information of a region in which some of lesion information is displayed on the guide image may correspond to each other.

The program may display a slice navigation tool in a display region associated with the identified 3D image slice. The program may perform navigation for 3D tomosynthesis images in the depth-wise direction by using the slice navigation tool.

The slice navigation tool may include an indicator for identifying each of the plurality of 3D image slices. For each of a plurality of pieces of lesion information displayed on the guide image, the program may display identification information of a focus slice and a lesion score for the corresponding lesion at a position corresponding to the indicator of the focus slice.

The program may set a partial region of the identified 3D image slices as an enlarged region and change the 3D image slice displayed in the enlarged region in response to a user input. Also, the program may display the identified 3D image slice in regions other than the enlarged region even if the enlarged region is changed to another 3D image slice.

The program may display a pre-stored medical image in response to selection of lesion information shown in the identified 3D image slice. The pre-stored medical image may be an image obtained by an external medical imaging device.

The program may navigate a focus slice corresponding to selected lesion information from among the plurality of 3D image slices in response to selection of some of a plurality of pieces of lesion information displayed on the guide image. Also, the program may display a navigated focus slice.

The program may record feedback notes in the guide image or the identified 3D image slice based on a user input. The program can store the feedback notes together with the guide image or the identified 3D image slice as a separate single image and transmit the single image to the second server. In detail, the program may generate a separate single image by merging the feedback notes in the form of an overlay on the guide image or the identified 3D image slice and transmit the single image to the second server.

The program may receive and display updated 3D tomosynthesis images from the second server, in response to the generation of a pre-set trigger signal again. The updated 3D tomosynthesis images may be 3D tomosynthesis images in which a plurality of 3D image slices and the single image are interlocked with each other.

Figure 12:
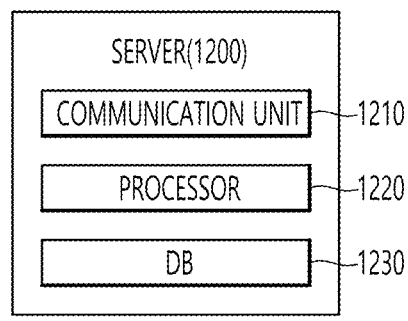
FIG. 12 is a block diagram showing a server according to an embodiment.

FIG. 12 is a block diagram showing a server according to an embodiment.

Referring to FIG. 12, a server 1200 may include a communication unit 1210, a processor 1220, and a database (DB) 1230. In the server 1200 of FIG. 12, only components related to embodiments are shown. Therefore, it may be understood by one of ordinary skill in the art that other general-purpose components may be further included in addition to the components shown in FIG. 12.

The communication unit 1210 may include one or more components for performing wired/wireless communication with an external server or an external device. For example, the communication unit 1210 may include at least one of a short-range communication unit (not shown), a mobile communication unit (not shown), and a broadcast receiving unit (not shown).

The DB 1230 is a hardware component for storing various data processed in the server 1200 and may store a program for processing and controlling the processor 1220.

The DB 1230 may include a random access memory (RAM), such as a dynamic random access memory (DRAM) and a static random access memory (SRAM), a read-only memory (ROM), an electrically erasable programmable read-only memory (EEPROM), a CD-ROM, a Blu-ray or other optical disk storage, a hard disk drive (HDD), a solid state drive (SSD), or a flash memory.

The processor 1220 controls the overall operation of the server 1200. For example, the processor 1220 may generally control an input unit (not shown), a display (not shown), the communication unit 1210, the DB 1230, etc. by executing programs stored in the DB 1230. The processor 1220 may control the operation of the server 1200 by executing programs stored in the DB 1230.

The processor 1220 may control at least some of the operations of the server 1200 described above with reference to FIGS. 1 to 11. The server 1200 may be the same as the second servers 120, 220, and 320 of FIGS. 1 to 3 or may be implemented as a device that performs some of the operations of the second servers 120, 220, and 320.

The processor 1220 may be implemented by using at least one from among application specific integrated circuits (ASICs), digital signal processors (DSPs), digital signal processing devices (DSPDs), programmable logic devices (PLDs), field programmable gate arrays (FPGAs), controllers, microcontrollers, microprocessors, and other electrical units for performing functions.

The server 1200 may be implemented as a computer device or a plurality of computer devices that communicate through a network to provide commands, codes, files, contents, services, etc.

Embodiments of the present disclosure may be implemented in the form of a computer program that can be executed through various components on a computer, and such a computer program may be recorded in a computer-readable recording medium. In this case, the recording medium may include a magnetic medium such as a hard disk, a floppy disk, and a magnetic tape, an optical recording medium such as a CD-ROM and a DVD, a magneto-optical medium such as a floptical disk, and hardware devices specially configured to store and execute program instructions such as a ROM, RAM, and a flash memory.

Meanwhile, the computer program may be specially designed and configured for the present disclosure or may be known and available to one of ordinary skills in the computer software field. Examples of computer programs may include machine language code such as code generated by a compiler, as well as high-level language code that may be executed by a computer using an interpreter or the like.

According to an embodiment, methods according to various embodiments of the present disclosure may be included and provided in a computer program product. The computer program product may be traded between sellers and buyers as commodities. The computer program products may be distributed in the form of a machine-readable storage medium (e.g., a compact disc read only memory (CD-ROM)), via an application store (e.g. PlayStore™), directly between two user devices, or online (e.g., downloaded or uploaded). In the case of online distribution, at least a portion of a computer program product may be temporarily stored or temporarily generated in a machine-readable storage medium such as a memory of a manufacturer's server, an application store server, or a relay server.

Operations constituting a method according to the present disclosure may be performed in an appropriate order, unless a particular order is explicitly stated or stated otherwise. The present disclosure is not necessarily limited to the order in which the operations are described. The use of all examples or exemplary terms (e.g., etc.) in the present disclosure is merely for the purpose of describing the present disclosure in detail, and the scope of the present disclosure is not limited by the examples or the exemplary terms unless defined by the claims. Also, one of ordinary skill in the art will appreciate that various modifications, combinations, and changes may be made in accordance with design conditions and factors within the scope of the appended claims or their equivalents.

Therefore, the spirit of the present disclosure should not be limited to the above-described embodiments, and not only the scope of claims below, but also all scopes equivalent to the claims or equivalent modifications therefrom will belong to the spirit of the present disclosure.

According to the above-described solutions of the present disclosure, by interlocking lesion location between a guide image and 3D tomosynthesis images including a plurality of 3D image slices, a user may quickly identify a lesion with minimal action. Also, by interlocking a lesion location between a guide image and 3D tomosynthesis images, it is possible to reduce reading time, improve accuracy, and reduce reader fatigue regarding lesion analysis.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A method of interlocking a lesion location between a guide image and 3D tomosynthesis images comprising a plurality of three dimensional (3D) image slices, the method comprising:
executing a program in response to generation of a pre-set trigger signal;
receiving, from a second server, a guide image which is a two dimensional (2D) medical image of a body part, and a plurality of 3D image slices constituting 3D tomosynthesis images of the body part;
simultaneously displaying the guide image showing a plurality of pieces of lesion information detected from the plurality of 3D image slices, and at least one 3D image slice included in the plurality of 3D image slices which shows a part of the plurality of pieces of lesion information;
in response to receiving a user input of selecting a piece of lesion information among the plurality of pieces of lesion information on the guide image, changing the at least one 3D image slice to a 3D image slice, among the plurality of 3D image slices, which has a highest lesion score for a lesion corresponding to the piece of lesion information,
wherein a lesion location is displayed on the 3D image slice and the guide image and interlocked between the 3D image slice and the guide image, and
wherein a lesion score for the lesion indicates a degree of confidence of an artificial intelligence (AI) model about the lesion being malignant in each 3D image slice.

2. The method of claim 1, further comprising:
identifying the at least one 3D image slice that is a focus slice in which a particular lesion is most clearly visible from among the plurality of 3D image slices.

3. The method of claim 1, wherein coordinate information of a region in which the piece of lesion information is displayed on the at least one 3D image slice corresponds to coordinate information of a region in which the piece of lesion information is displayed on the guide image.

4. The method of claim 1, wherein
the displaying further comprises displaying a slice navigation tool in a display region of the 3D image slice, and
the method further comprises performing navigation for the 3D tomosynthesis images in a depth-wise direction based on a user input received on the slice navigation tool.

5. The method of claim 4, wherein
the slice navigation tool comprises an indicator for identifying each of the plurality of 3D image slices, and
for each of the plurality of pieces of lesion information displayed on the guide image, identification information of a focus slice in which a corresponding lesion is most clearly visible from among the plurality of 3D image slices, and a lesion score of the corresponding lesion in the focus slide are displayed at a position corresponding to the indicator of the focus slice.

6. The method of claim 1, further comprising:
enlarging a partial region of the at least one 3D image slice; and
changing the enlarged region to another 3D image slice in response to a user input of changing the enlarged region,
wherein the at least one 3D image slice is maintained in regions other than the enlarged region even if the enlarged region is changed.

7. The method of claim 1, wherein
the displaying further comprises displaying a pre-stored medical image in response to selection of the piece of lesion information on the 3D image slice, and
the pre-stored medical image is obtained by an external medical imaging device.

8. The method of claim 1, further comprising:
recording feedback notes in the guide image or the at least one 3D image slice based on a user input;
generating a separate single image by merging the feedback notes in the form of an overlay on the guide image or the at least one 3D image slice; and
transmitting the single image to a first server or the second server.

9. The method of claim 8, further comprising
receiving and displaying updated 3D tomosynthesis images from the first server or the second server when the pre-set trigger signal is generated again,
wherein the updated 3D tomosynthesis images include the plurality of 3D image slices and the single image which are interlocked with each other.

10. An apparatus for interlocking a lesion location between a guide image and 3D tomosynthesis images comprising a plurality of 3D image slices, the apparatus comprising:
a memory in which at least one program is stored; and
at least one processor operated by executing the at least one program,
wherein the at least one processor is configured to
execute a program in response to generation of a pre-set trigger signal,
receive, from a second server, a guide image which is a 2D medical image of a body part, and a plurality of 3D image slices constituting 3D tomosynthesis images of the body part,
simultaneously display the guide image showing a plurality of pieces of lesion information detected from the plurality of 3D image slices, and at least one 3D image slice included in the plurality of 3D image slices; which shows a part of the plurality of pieces of lesion information, and
in response to receiving a user input of selecting a piece of lesion information among the plurality of pieces of lesion information on the guide image, change the at least one 3D image slice to a 3D image slice, among the plurality of 3D image slices, which has a highest lesion score for a lesion corresponding to the piece of lesion information,
wherein a lesion location is displayed on the 3D image slice and the guide image and interlocked between the at least one 3D image slice and the guide image, and
wherein a lesion score for the lesion indicates a degree of confidence of an artificial intelligence (AI) model about the lesion being malignant in each 3D image slice.

11. A non-transitory computer-readable recording medium having recorded thereon a program for executing the method of claim 1 on a computer.

* * * * *